United States Patent [19]

McGrath

[11] 4,105,036

[45] Aug. 8, 1978

[54] PORTABLE SAUNA

[76] Inventor: Joseph Michael McGrath, 51 Black Rock Pl., Holland, Pa. 18966

[21] Appl. No.: 722,113

[22] Filed: Sep. 10, 1976

[51] Int. Cl.² .............................................. A61N 33/06

[52] U.S. Cl. .................................................. 128/374

[58] Field of Search ............... 128/367, 371, 374, 293; 4/160, 164

[56] References Cited

U.S. PATENT DOCUMENTS

| | | | |
|---|---|---|---|
| 261,598 | 7/1882 | Goldberg | 128/371 |
| 1,059,505 | 4/1913 | Tuttle | 128/374 |
| 2,814,297 | 11/1957 | Stewart | 128/374 |
| 3,246,645 | 4/1966 | Kerns et al. | 128/374 |
| 3,419,915 | 1/1969 | Clark | 128/293 X |
| 3,772,713 | 11/1973 | Roullier | 4/164 |

FOREIGN PATENT DOCUMENTS

| | | | |
|---|---|---|---|
| 83,884 | 9/1964 | France | 128/374 |

*Primary Examiner*—Lawrence W. Trapp

*Attorney, Agent, or Firm*—Weiser, Stapler & Spivak

[57] ABSTRACT

The present invention relates to a portable, flexible, heating unit in the nature of a sauna, which derives its heat and moisture from external sources.

4 Claims, 2 Drawing Figures

PORTABLE SAUNA

BACKGROUND OF THE INVENTION

The present invention relates in general to sauna devices, and more particularly, to a portable, flexible, individual sauna which derives its heat and moisture from external sources.

The use of saunas, steam rooms and the like for therapeutic and recreational benefit has long been known. Commonly, these take the form of room size units having capacity for many persons and being integrated as a fixed element of a building or as the only occupancy of an entire building. The prior art types of saunas are unsuited to use by individuals in the privacy of their homes and are thus less convenient than they might otherwise be desired. Recognizing this, the art has progressed to the production of individual "steam box" type units which are generally shaped as an enclosure in which a seat such as a stool may be placed. The "steam box" type of units are rigid and have a door on the front which opens to allow the user to enter. Such units have usually been designed with a self-contained heating source and, as before mentioned, are rigid in their construction. Other prior art devices have been permanently connected to other sources of heat such as a steam line to provide the elevated temperatures required for satisfactory operation. These units, although more adaptable to the use of individuals without the necessity of travelling to centralized locations, have the draw backs of being cumbersome, space consuming and expensive, as well as requiring permanent installation.

The long known use of sweat suits by athletes and those wishing to lose weight, has resulted in the development of various body suits which are fabricated of heat reflective and moisture retentive material, including sheet plastics, woven nylon and the like. While such sweat suits have the benefits of being more convenient and less expensive than the previously described devices, these "suits" are limited in the amount of heat which can be retained, whether wet or dry and by the fact that they contain no provision for external sources of heat. Thus, it is evident that their therapeutic value is inherently limited.

SUMMARY OF THE INVENTION

The present invention relates generally to the field of heat and moisture retention devices, and more particularly is directed to a portable sauna of flexible construction suitable for use with a readily available source of heat.

The portable sauna of the present invention comprises generally a flexible, portable enclosure of suitable size and shape to facilitate entrance of a single user. The portable sauna is fabricated of a moisture proof material, such as sheet plastic, and includes an opening through which heat and moisture from an external source can be admitted into the interior of the enclosure.

It is contemplated that the device can be satisfactorily and economically operated by tapping a readily available source of heat that is present in most houses in abundant supply. In most instances, the usual household laundry drying machine that is installed to automatically dry the wash, is equipped with a vent of suitable size to carry the waste products of the drying operation to a point of disposal. The waste products of the drying cycle comprise heat and moisture which are entirely clean and which are therefore normally vented exteriorly of the building without fear of air pollution. In the present situation, part or all of the effluent of the dryer is introduced into the portable sauna through the opening to thereby provide a clean, convenient and "free" supply of energy.

Because of the flexible nature of the sauna enclosure materials and the fact that the heat source can be readily connected and disconnected, it is contemplated that the device will be disconnected when not in use and then stored in a folded condition to conserve space.

It is a primary object of the present invention to provide an individual sauna or heating compartment that is fully collapsible and which includes means for receiving an external source of heat.

It is another object of the present invention to provide an individual, flexible compartment having means for connection to a source of inexpensive, clean, moist heated air.

It is a further object of the invention to provide a compartment having means for connection to a source of clean, moist heated air, such as the effluent from a conventional home dryer as a source of external heat for the compartment.

It is another object of the present invention to provide a novel, portable sauna having flexible, moisture proof sheet plastic panels and which includes a moist heat inlet and an exhaust air vent.

It is another object of the present invention to provide a novel portable sauna that is simple in construction, inexpensive in manufacture and trouble-free when in use.

Other objects and a fuller understanding of the invention will be had by referring to the following description and claims of a preferred embodiment thereof, taken in conjunction with the accompanying drawings, wherein like reference characters refer to similar parts throughout and in which:

DESCRIPTION OF THE PREFERRED EMBODIMENT OF THE INVENTION

Figure 1:
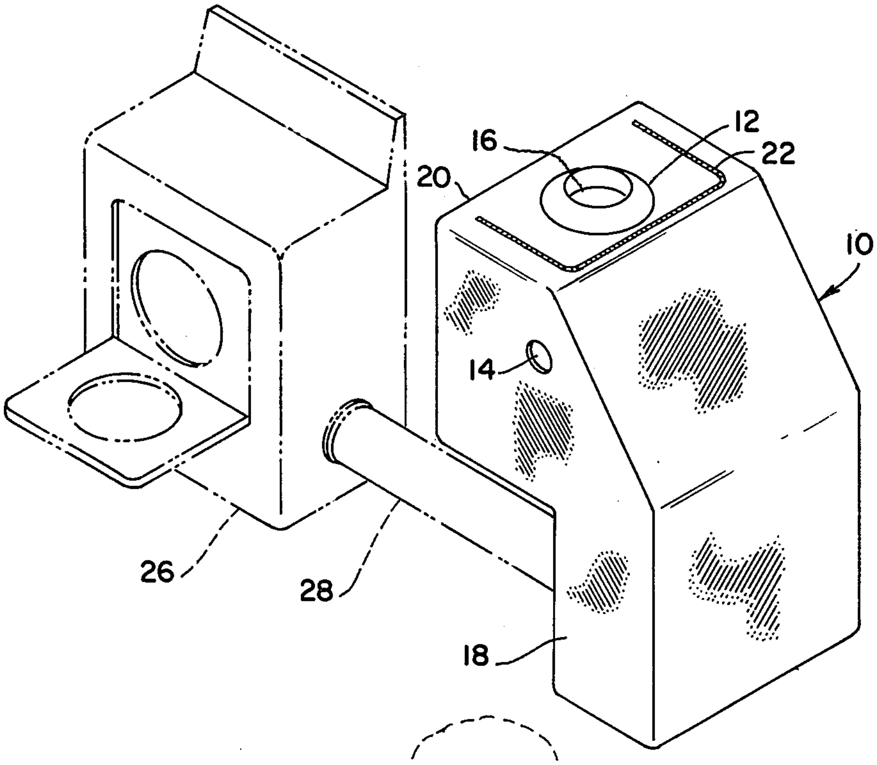
FIG. 1 is a perspective view of the apparatus showing its preferred association with an external heating means.

Although specific terms are used in the following description for the sake of clarity, these terms are intended to refer only to the particular structure of the invention selected for illustration in the drawings, and are not intended to define or limit the scope of the invention.

As shown in FIG. 1, the sauna comprises a compartment 10 which is designed and configured to accommodate an individual user, usually in the seated position. When so seated, the head of the user 24 extends through a collar 12 which defines the head opening 16. The collar preferably is fabricated of a material, such as foam rubber or turkish toweling which is comfortable to the user and which substantially prevents the escape of the heated moist air from the compartment. A vent 14 permits the controlled escape of heated air for the purpose of maintaining a continuous turn-over flow of air in the compartment and the maintenance of a continuous pressure therein. The diameter of the vent outlet opening 14 should be smaller than the diameter of the heated, moist air inlet opening 32 (FIG. 2) for pressure maintenance purposes. The pressure of the heated air from the dryer 26 is utilized to inflate the compartment 10 to form a hollow enclosure. A closure 22, which may be in the form of a conventional plastic zipper, permits access to the inside of the compartment 10 and is conveniently located so as to be usable by persons of different sizes. As illustrated the closure is positioned at the top of the compartment and defines an access panel of sufficient size to allow easy access into the compartment interior.

The heating access opening 32 is preferentially located on the rear panel of the base 18 of the compartment 10 and can be removably fitted with a connecting means 28 for associating the compartment 10 with a source of external heat, for example, a conventional domestic gas or electric dryer 26.

While the advantages of the present invention are readily apparent, it should be stressed that the use of clean, moist heat derived from a source, such as a conventional home clothes dryer 26 which would ordinarily be wasted, provides the user 24 of the present invention with substantially unlimited source of energy at no additional expense. Thus, in this preferred embodiment of the invention wherein the source of heat is as indicated, particularly provides a surprising use for a source of energy heretofore untapped in this manner.

Another aspect of the inventive concept which is particularly important is the convenience of use and limited storage space requirements of the compartment due to its construction from flexible, moisture-proof materials, such as sheet vinyl or woven nylon. Thus, the present invention provides an improved therapeutic and/or recreational device over that which has previously been available. The advantages of flexibility, convenience and inexpensive contruction are combined with the enhanced effect derived from the use of external heating means wherein heat that heretofore would have been wasted can now be conveniently utilized.

In order to use the compartment 10 of the present invention as a portable sauna, the clothes dryer should be operated in the usual manner to cause warm, moist air to be expelled from the dryer 26. The dryer vent is disconnected from the usual exhaust stack, and in lieu thereof, is interconnected with the connecting means 28. The connecting means 28 may be a rigid or flexible conduit and constructed of conventional materials such as bent sheet metal or suitably formed plastic. The conduit 28 interconnects the compartment inlet air opening 32 with the dryer vent in a substantially airtight manner so that hot, moist air that is expelled from the dryer 26 enters the interior of the compartment 10 without loss.

Figure 2:
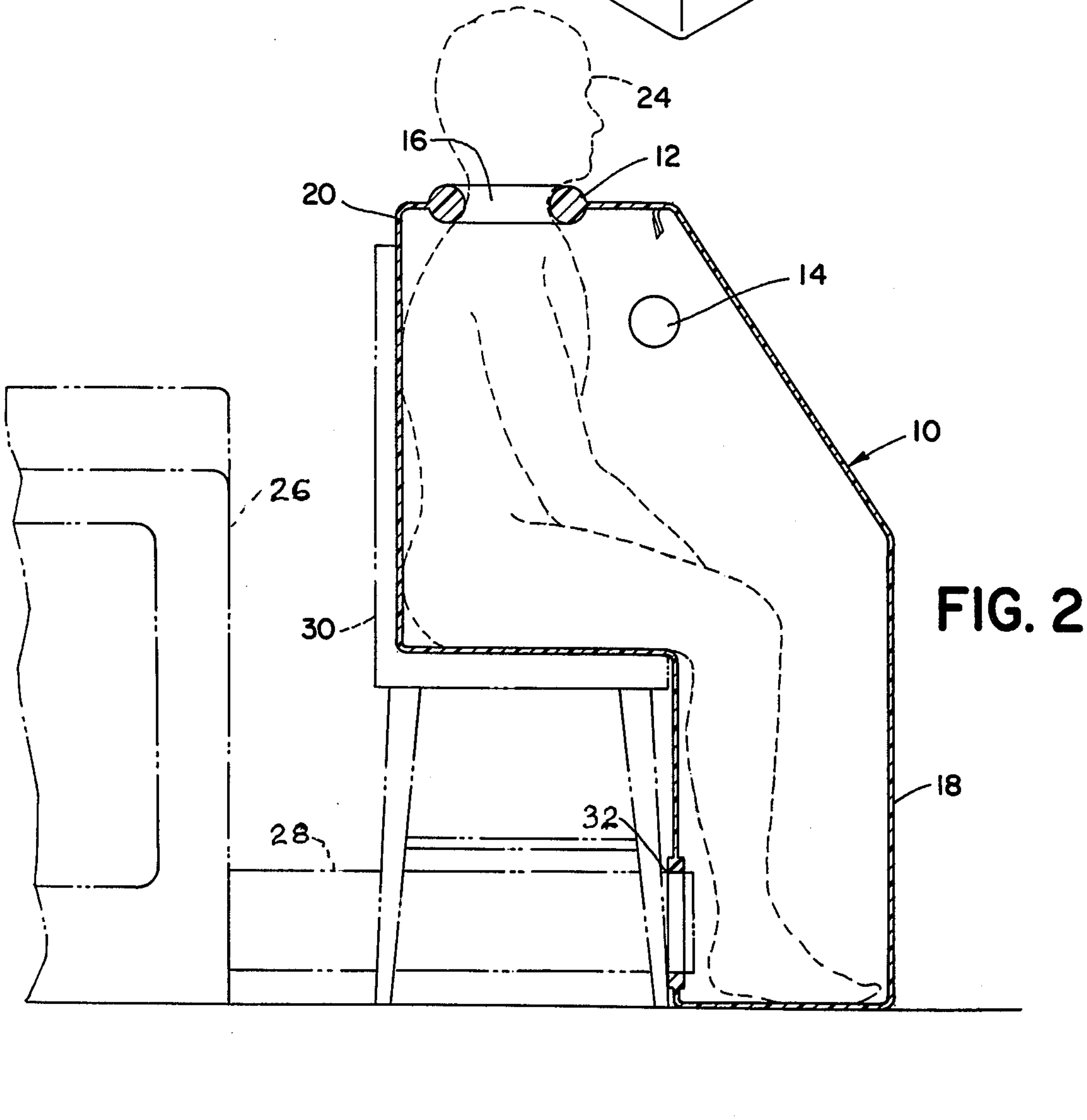
FIG. 2 is a cross sectional view of the present apparatus showing its association with both external heating means and with the occupant user.

As best seen in FIG. 2, the compartment 10 comprises a relatively narrow base section 18 of suitable configuration to enclose the legs of the user 24 and a relatively wide upper section 20 to enclose the upper torso of the user. In a preferred embodiment, the compartment is fabricated of offset configuration to enable the user 24 to conveniently be seated during the treatment period on an exterior positioned chair 30 or the like.

With the conduit 28 properly interconnecting the dryer 26 to the compartment 10 at the warm air inlet opening thereof, and with the chair 30 conveniently positioned, the user 24 can enter the interior of the compartment through the upper access panel by opening the zipper 22 and stepping inside. The user positions his head through the opening 16 and places the collar 12 comfortably about his neck. The user 24 can then be seated as illustrated and the closer 22 is functioned from the compartment interior to close the upper access panel. As hereinbefore set forth, a greater volume of air is admitted into the compartment interior through the air inlet opening 32 than is allowed to escape through the compartment vent opening 14. In this manner, the compartment is continually pressurized to provide a comfortable, portable sauna of lightweight, flexible construction.

Although the present invention has been described with reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto.

What is claimed is:

1. A portable sauna comprising a user compartment which is characterized by flexible compartment sidewalls and by the introduction of heat and moisture from an external source into the compartment interior, said compartment being pressurized by the outside source to an inflated condition; said source being clean, moist, heated air, said air being adapted to heat the compartment interior and to inflate the compartment, said external source being a conventional home clothes dryer; and means for connecting a conduit, said conduit leading the air from exteriorly of the compartment to the compartment interior.

2. The sauna according to claim 1 wherein the compartment has no rigid structure, the said sidewalls defining a relatively wide upper section and a relatively narrow base section, the upper and base sections interconnecting to define an interior space within which the user can position himself, a portion of the upper section being laterally offset from the base section and is adapted to form a seating area fro the user of the sauna.

3. A portable sauna comprising a user compartment which is characterized by the introduction of heat and moisture from an external source into the compartment interior and wherein the external source is a conventional home clothes dryer.

4. The sauna according to claim 2 and an exteriorly positioned chair, the seating area of the sauna being adapted to rest upon the chair whereby the user can sit upon the seating area and be supported by the chair.

* * * * *